US005606107A

United States Patent [19]
Smith

[11] Patent Number: 5,606,107
[45] Date of Patent: Feb. 25, 1997

[54] FORMIC ACID AND FORMALDEHYDE DESTRUCTION IN WASTE STREAMS

[75] Inventor: Lowell R. Smith, St. Louis, Mo.

[73] Assignee: Monsanto Company, St. Louis, Mo.

[21] Appl. No.: 474,583

[22] Filed: Jun. 7, 1995

[51] Int. Cl.$^6$ .................................. C02F 1/68; C07F 9/28
[52] U.S. Cl. .......................... 562/17; 210/762; 210/763; 210/908; 423/437 R
[58] Field of Search ...................................... 210/762, 763, 210/908; 423/437 R; 562/17

[56] References Cited

U.S. PATENT DOCUMENTS

| | | | |
|---|---|---|---|
| 3,804,756 | 4/1974 | Callahan et al. | 210/763 |
| 4,093,543 | 6/1978 | Rodewald et al. | 210/763 |
| 5,205,906 | 4/1993 | Grutsch et al. | 210/763 |
| 5,244,581 | 9/1993 | Murphy | 210/763 |
| 5,460,734 | 10/1995 | Birbara et al. | 210/763 |

FOREIGN PATENT DOCUMENTS

| | | |
|---|---|---|
| 539300 | 4/1957 | Canada . |
| 3439643 | 4/1986 | Germany ........................ 423/580.1 |

*Primary Examiner*—Wayne Langel
*Attorney, Agent, or Firm*—Grace L. Bonner; Mark F. Wachter; Arnold, White & Durkee

[57] ABSTRACT

A process is provided for destroying formic acid and/or formaldehyde in an aqueous, organic acid waste stream by contacting the stream with a supported precious metal catalyst and passing air or molecular oxygen gas through the solution to promote chemical oxidation. The invention is a safe, practical and cost-effective alternative to bio-system treatment of these compounds using microorganisms. The process of the invention may be practiced in either a batch or continuous mode and, in accordance with the invention, formic acid present in a stream at a level of 3800 ppm and formaldehyde present in an amount of 5800 ppm can be reduced respectively to levels of 200 ppm or less.

25 Claims, No Drawings

FORMIC ACID AND FORMALDEHYDE DESTRUCTION IN WASTE STREAMS

BACKGROUND

1. Field of the Invention

This invention involves the efficacious treatment of an aqueous stream containing governmentally regulated formic acid and/or formaldehyde.

More particularly, this invention relates to a process for destroying formic acid and/or formaldehyde in an aqueous waste stream by precious metal-catalyzed oxidation.

2. Description of the Related Art

It is believed that the present invention can be practiced, generally, in conjunction with aqueous streams containing formic acid and/or formaldehyde.

Given its potential for broad application, the present invention has been shown to have particular advantageous application in treating the formic acid and formaldehyde-containing waste stream generated in connection with the manufacture of N-phosphonomethyl-glycine.

N-phosphonomethylglycine, which is known in the agricultural chemical industry as glyphosate or glyphosate acid, is a highly effective and commercially important herbicide useful in controlling the growth of germinating seeds, emerging seedlings, maturing and established woody and herbaceous vegetation, and aquatic plants.

Glyphosate and its salts are conveniently applied in an aqueous formulation as a broad-spectrum (i.e. effective on a wide variety of plants), post-emergent herbicide. (i.e. effective on a wide variety of plants), post-emergent herbicide.

Various methods are known in the art for the preparation of N-phosphonomethylglycine and its intermediate composition N-phosphonomethylimino-diacetic acid.

For example, in U.S. Pat. No. 4,724,103 to Gentilcore a process for preparing N-phosphonomethyliminodiacetic acid (glyphosate intermediate) is disclosed. This process involves sequentially reacting an alkali metal salt of iminodiacetic acid with a strong mineral acid to form the strong mineral acid salt of iminodiacetic acid and the alkali metal salt of the strong mineral acid and phosphonomethylating the iminodiacetic acid by reaction with formaldehyde and phosphorous acid to provide a mixture of N-phosphonomethyliminodiacetic acid and an alkali metal salt.

Also involved in the process is a step by which the desired intermediate product is separated from other reaction products leaving a formaldehyde-containing waste solution that is readily treatable in accordance with the process of the present invention when formaldehyde and formic acid are distilled out of the heavy organic waste stream by overhead evaporation.

In U.S. Pat. No. 3,969,398 to Hershman, a process is disclosed for the production of N-phosphonomethylglycine by the oxidation of N-phosphonomethyliminodiacetic acid utilizing a molecular oxygen-containing gas as the oxidant in the presence of a catalyst comprising activated carbon.

Characteristic of glyphosate production, such as in this process, there is often provided a conventional distillation step whereby a formic acid and formaldehyde-containing overhead waste stream is formed when these undesirables are separated from the desired N-phosphonomethylglycine product as by distillation.

The liquid waste stream thus formed is a solution containing significant amounts of formaldehyde and formic acid which are substances that cause toxicological concern and are suspected carcinogens.

Eliminating the formaldehyde and formic acid from this stream in high yields is, thus, desirable.

The present invention provides a technically simple and direct process, whereby substantially all of the formic acid and formaldehyde in an aqueous organic stream and, particularly, in waste streams obtained in connection with the production of N-phosphonomethyliminodiacetic acid (i.e. glyphosate intermediate) and N-phosphonomethylglycine or glyphosate acid are eliminated.

This disproportionately high oxidation/conversion of formaldehyde into formic acid and formic acid, in turn, to carbon dioxide and water occurs surprisingly fast and efficiently in connection with the process of the present invention.

SUMMARY OF THE INVENTION

In accordance with the practice of the present invention, an aqueous waste stream containing unreacted formic acid and/or formaldehyde is treated by oxidation catalyzed by a supported precious metal catalyst.

In a particular embodiment formaldehyde and formic acid, each present in a representative aqueous waste stream in respective amounts of approximately 6000 ppm and 4000 ppm, are generated from the manufacture of N-phosphonomethylglycine by the reaction of N-phosphonomethyliminodiacetic acid, water and oxygen. In accordance with the invention disclosed herein, these materials are each substantially eliminated and reduced to a commercially innocuous and acceptable level of 200 ppm or less in which case the stream is rendered suitable for recycling.

The novel and useful method of the present invention is amenable for being practiced in either a batch format or as a continuous process. Further, while various supported metal catalysts may be employed in the practice of the invention and particularly those supported catalysts containing any one of the metals selected from Group VIII as contained in the Periodic Table of Elements, a heterogeneous Pt on carbon catalyst is the preferred catalyst for carrying out the process of the invention.

Adherence to certain process variables in accordance with the invention including temperature, pressure and the level of dissolved air or oxygen in the solution being treated is also important in obtaining maximum advantage from the invention.

When compared to the alternative bio-treatment of undesirable formaldehyde and/or formic acid, several significant advantages are believed to inure to the process of the present invention. In particular, catalytic oxidation of these undesirables is considered less capital intensive. Also, it avoids the generation of bio-sludge and, very significantly, where evaporator overhead streams are treated in accordance with the present invention, a substantially undesirable-free aqueous stream can be generated suitable for recycling back through the original process.

DETAILED DESCRIPTION OF THE INVENTION

As indicated above, the present invention may be practiced in conjunction with eliminating formaldehyde and formic acid, generally, from aqueous organic streams.

However, because these undesirable compounds are produced in connection with the manufacture of N-phosphonomethylglycine, and because the present invention has been found to be particularly useful in treating waste streams produced in connection therewith, reference will be made to an embodiment of the invention in which formaldehyde and formic acid are destroyed in effluent from the production of N-phosphonomethylglycine. Thus, it is in this context that the description below will fully disclose the invention and describe its mode of operation with particularity.

Considerable quantities of formic acid and formaldehyde are generated as waste products, for example, in the manufacture of N-phosphonomethylglycine. The destruction of formic acid and/or formaldehyde in waste streams is required to reduce the emissions of these potentially toxic and governmentally regulated materials.

Presently, these compounds are typically separated from process streams by either evaporation or ion exchange and then destroyed in bio-treatment facilities using biological treatments such as by microorganisms.

A waste stream containing undesirably high levels of formaldehyde and formic acid which the practice of the present invention converts into environmentally acceptable products is generated by the practice of the processes disclosed in U.S. Pat. Nos. 4,724,103 and 3,969,398.

In the former process, disodium iminodiacetate (DSIDA) and phosphorus trichloride ($PCl_3$) are heated together in water to an elevated temperature to yield a slurry of the hydrochloride of iminodiacetic acid, sodium chloride and phosphorous acid. Thereafter, $CH_2O$ (as formalin) is slowly added. The resulting reaction mixture is cooled. An aqueous solution of sodium hydroxide is then added in an amount sufficient to minimize the solubility of N-phosphonomethylimino-diacetic acid which precipitates from solution. The mixture is filtered or centrifuged and the resulting solid material is recovered. The resulting liquid from the isolation of N-phosphonomethyliminodiacetic acid is a waste stream containing, among other things, potentially toxic formaldehyde and formic acid, selected organic phosphonic acids, sodium chloride and selected mineral acids of phosphorus.

When undesirable formaldehyde and formic acid are distilled out of this heavily organic stream such as by distillation to form a second waste stream, the practice of the present invention converts the second formaldehyde and formic acid-containing stream into a predominant mixture of environmentally benign carbon dioxide and water. Thus, the stream is rendered more suitable for either disposal or, where an overhead stream is treated, for recycling back through the underlying process.

In accordance with the process of the present invention formaldehyde and/or formic acid are catalytically oxidized and, thus, eliminated from aqueous waste streams containing these undesirable compounds.

Catalytic oxidation as carried out in accordance with the process of the invention involves the treatment of a formaldehyde and/or formic acid-containing aqueous stream with a supported metal catalyst in the presence of dissolved oxygen or oxygen-containing air.

The preferred catalyst support material is carbon and the metal for loading in the catalyst is selected from among the Group VIII metals. Further, the basic chemistry involved in the process is as follows:

1. 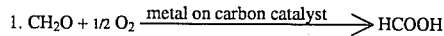 $CH_2O + 1/2 O_2 \xrightarrow{\text{metal on carbon catalyst}} HCOOH$ 2. 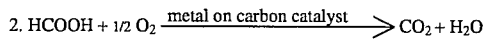 $HCOOH + 1/2 O_2 \xrightarrow{\text{metal on carbon catalyst}} CO_2 + H_2O$ Reaction 1 shows that, when oxidized in accordance with the present invention, formaldehyde converts to formic acid and reaction 2 shows that formic acid, in turn, is converted to environmentally benign carbon dioxide and water.

In a broad sense, the reactions shown above may be practiced in accordance with the present invention in any conventional reactor at room temperature and atmospheric pressure. The reaction can be carried out in a suitable reactor at a pressure from atmospheric to about 200 psi and the stream which is treated can be heated to a temperature of between about 50° C. and about 90° C. Furthermore, provided that a suitable level of oxygen or oxygen-containing air is dissolved in the stream being treated, any of the Group VIII metals may be employed in the practice of the invention.

In order to obtain the maximum advantage from the invention, however, and to make it particularly useful in a commercial context the adherence to certain process limitations in accordance with the invention is required.

In this regard, while any conventional reactor system may be employed to practice the invention, one suitable for pressurized operation and having a good agitation character is preferred. These features of the suitable reactor will enable the invention to be practiced more efficiently because agitation and pressure facilitate the dissolution of oxygen or oxygen-containing air into the waste stream—the concentration of which affects catalytic activity as alluded to above.

In a similar manner, the choice of the particular Group VIII metal and the amount of its loading to the carbon support or substrate will also affect the rate of the oxidation reaction and, thus, the relative commercial advantage obtained in practicing the invention. The inventor has discovered that, from the Group VIII metals, palladium (Pd), rhodium (Rh) and particularly platinum (Pt) function most desirably in conjunction with the invention. For this reason, platinum is the preferred metal loading for the catalyst and is, therefore, referenced in the data that comprise this disclosure.

The catalyst may contain platinum in the range of about 0.1 wt. % to about 10 wt. % as long as the total ratio of platinum to the working reactor volume is in the range of about 0.00015 to 1 up to about 0.00040 to 1.

Those skilled in the art will recognize that, while the remaining group VIII metals may be employed in this invention, they will lead to slower reaction rates unless employed in larger amounts.

Those skilled in the art will appreciate that comparatively high loadings of the selected metal in the catalyst are likely to result in an improved degree and rate of reaction and, thus, may be preferred over lower loadings. The cost of the catalyst, however, is often a factor in its selection and, where as here, the preferred metal loading is comprised of a precious and expensive metal such as platinum an obvious advantage exists in identifying optimum catalyst loadings for use in the present invention. Thus, based upon the teachings provided herein, those skilled in the art will be able to determine such optimal catalyst. A compromise must be made between practical reaction rates and catalyst cost.

As indicated above, a suitable reactor for use in conjunction with the present invention should have a good agitation feature. Agitation is instrumental in aiding the dissolution of oxygen which is critical to the successful practice of the invention. For example, it has been found that when the concentration of dissolved oxygen is too low, incomplete reaction occurs. Surprisingly, and obversely, too high a concentration of dissolved oxygen is also deleterious to the process of the invention. More specifically, it has been found that the optimum dissolved concentration of oxygen is in the range of about 1–7 ppm. When the process of the invention is operated having a dissolved oxygen concentration outside these limits, in the case of continuous mode - the oxidation reaction is not completed and in the batch mode a longer time is required to complete the reaction. Thus, it is clear that to ensure this concentration of dissolved oxygen in accordance with the process of the invention, the interaction between oxygen and/or oxygen contain air flow rate and agitation must be considered.

An analysis of a typical waste stream such as one obtained from the manufacture of N-phosphonomethylglycine prior to treatment in accordance with one embodiment of the present invention is as follows:

| Component | Weight Percent |
|---|---|
| Water | 99.1 |
| Formic acid | 0.4 |
| Formaldehyde | 0.6 |

EXAMPLES 1–3

The process described above was carried out under a variety of reaction conditions with various waste streams having been obtained from the production of N-phosphonomethylglycine generally in accordance with the process of U.S. Pat. No. 3,969,398. Each waste stream contained relative concentrations of formaldehyde and formic acid of approximately 6000 ppm/0.6 wt % and approximately 4000 ppm/0.4 wt. % respectively. The stream temperature while in the reactor varied from about 50° C. to about 90° C. The concentrations of formaldehyde and formic acid in the streams before and after each treatment were noted. The data from representative testing have been tabulated below.

All tests were performed in a continuous mode for up to 30 hours. The catalyst employed in these tests was 1.659 g of a Degussa F199XKYA/W, assaying at 4.49 wt. % Pt equivalent to 32 mg of Pt. Reactor volume was 120 g. and reactor pressure was 100 psi. Reactor temperature was maintained at 90° C. and the liquid feed rate was 6.0 g/min. The oxygen feed rate was 100 cc/min. and agitator speed was 1000 rpm. Data were collected every hour to ensure steady state conditions were maintained during the tests. An in-line FTIR was utilized for measuring the concentrations of formaldehyde and formic acid during the course of each run. It can be appreciated by those skilled in the art that this process can be readily scaled up for commercial use without loss of its advantages or efficiency.

TABLE 1

| | Length of run (Min.) | Effluent Formaldehyde, ppm Average Conc. | Formaldehyde End Conc. in ppm |
|---|---|---|---|
| 1. | 1728 | 32 | 0 |
| 2. | 1205 | 41 | 18 |
| 3. | 821 | 51 | 0 |

The average formaldehyde effluent concentration, as indicated in the above Table 1 was calculated by averaging all of the formaldehyde concentration data compiled throughout the duration of the test run.

Based upon experimentation, it was observed that formic acid effluent concentrations were lower than formaldehyde concentrations. Thus, formic acid concentrations were not routinely analyzed.

The information above is illustrative of the efficient manner in which the present invention may be operated continuously. However, the process of the invention may also be performed advantageously under batch conditions.

For example, in one autoclave reactor having a working volume of 120 ml., a slurry of 0.4 wt % of a 5 wt. % Pt. on carbon catalyst oxidized 5800 ppm of formaldehyde and 3800 ppm of formic acid in a solution to trace levels within 35 minutes or less. Temperatures during the reactions ranged from about 55° C.–90° C. and pressure was either 100 or 150 psig. Oxygen flow rates were 25 or 100 cc/min. Surprisingly, the greatest rate differences were observed in connection with oxygen flow rate changes rather than with changes in temperatures or pressure.

The in-situ chemical conversion of the formaldehyde into formic acid and formic acid, in turn, to carbon dioxide and water as provided by the practice of the present invention has proved to be a most cost effective alternative to biotreatment elimination of formaldehyde and/or formic acid from aqueous waste streams.

Due to the catalytic nature of the reaction, a continuous-mode process requiring a relatively short residence time of about 20 minutes has been demonstrated to be technically feasible for the destruction of substantially all of the formaldehyde and formic acid to form environmentally benign carbon dioxide and water in an aqueous solution suitable for recycling.

The environmental compatibility of the product resulting from the practice of the present invention has thus, been demonstrated.

While the illustrative embodiments of the invention have been described with particularity, it will be understood that various other modifications will be apparent to and can be readily made by those skilled in the art without departing from the spirit and scope of the invention.

Accordingly, it is not intended that the scope of the claims appended hereto be limited to the examples and description as set forth hereinabove but rather that the claims be construed as encompassing all the features of patentable novelty which reside in the present invention, including all features which would be treated as equivalents thereof by those skilled in the art to which the invention pertains.

What we claim is:

1. A method for destroying formaldehyde and formic acid present in a liquid aqueous stream by converting formaldehyde to formic acid and converting formic acid to carbon dioxide and water, said method comprising the steps of:

(a) contacting said liquid stream with a supported Group VIII metal catalyst at a temperature in the range from room temperature to about 90° C. and at a pressure in the range from atmospheric to about 200 psi; and (b) introducing air or molecular oxygen into said liquid stream to achieve and maintain the concentration of dissolved oxygen in the range of about 1–7 ppm in the vicinity of said catalyst so as to oxidize a desired amount of formaldehyde to formic acid and formic acid to carbon dioxide and water.

2. The method of claim 1 wherein the Group VIII metal is selected from the group consisting of platinum, palladium and rhodium.

3. The method of claim 1 wherein the catalyst is heterogeneous platinum loaded on a powdered carbon support.

4. The method of claim 2 wherein said oxidation is carried out at a pressure of from atmospheric to about 150 psi and wherein said stream is heated to a temperature in the range of about 50° C. to about 90° C. during oxidation.

5. The method of claim 1 wherein formaldehyde is converted to formic acid and formic acid is converted to carbon dioxide and water at atmospheric pressure and at a temperature in the range from about 50° C. to about 90° C.

6. The method of claim 1 further comprising agitating said stream to achieve and maintain a level of dissolved oxygen within the range of about 1 ppm to about 7 ppm during oxidation.

7. The method of claim 1 wherein the Group VIII metal is platinum.

8. The method of claim 3 wherein the amount of platinum in the catalyst is in the range from about 0.1 wt % to about 10 wt %.

9. The method of claim 1 wherein the pressure is atmospheric.

10. The method of claim 1 wherein the temperature is room temperature.

11. The method of claim 9 wherein the temperature is room temperature.

12. In a process for the manufacture of N-phosphonomethyliminodiacetic acid of the type that produces acidic aqueous waste stream containing organic waste comprising formaldehyde, formic acid and other wastes, the improvement comprising the following steps:

(a) subjecting said waste stream to distillation to form a second stream including formaldehyde and formic acid;

(b) contacting said second stream with a catalyst comprising a Group VIII metal supported on a catalyst support; and (c) introducing air or molecular oxygen into said second stream to achieve and maintain the concentration of dissolved oxygen in the range of about 1–7 ppm in the vicinity of said catalyst so as to oxidize a desired amount of formaldehyde to formic acid and formic acid to carbon dioxide and water.

13. The method claim 12 wherein said metal is selected from the group consisting of platinum, palladium and rhodium.

14. The method of claim 12 wherein the metal in said catalyst is platinum loaded on powdered carbon in an amount of about 0.1 wt. % to about 10 wt %.

15. The method of claim 12 wherein the oxidation is carried out at a pressure of from atmospheric to about 200 psi and wherein said second stream is heated to a temperature of between about 50° C. to about 90° C.

16. The method of claim 12 wherein formaldehyde is converted to formic acid and formic acid is convened to carbon dioxide and water at atmospheric pressure and at a temperature in the range from about 50° C. about 90° C.

17. The method of claim 12 further comprising agitating said second stream to achieve and maintain a level of dissolved oxygen with the range of about 1 ppm to about 7 ppm.

18. The method of claim 13 wherein said metal on said supported catalyst is platinum, said platinum being supported on powdered carbon.

19. A method of treating an aqueous stream containing formaldehyde and formic acid wastes associated with the manufacture of N-phosphonomethylglycine comprising the steps of:

(a) contacting said stream with a catalyst comprising a Group VIII metal supported on a catalyst support; and (b) introducing air or molecular oxygen into said stream to achieve and maintain a concentration of dissolved oxygen in the range of about 1–7 ppm in the vicinity of said catalyst so as to oxidize a desired amount of formaldehyde to formic acid and formic acid to carbon dioxide and water.

20. The method of claim 19 wherein said metal is selected from the group consisting of platinum, palladium and rhodium.

21. The method of claim 19 wherein the metal is platinum loaded on powdered carbon in an amount of about 0.1 wt. % to about 10 wt %.

22. The method of claim 19 wherein the oxidation is carried out under a pressure of from atmospheric to about 200 psi and wherein said stream is heated to a temperature of between 50° C. to about 90° C.

23. The method of claim 19 wherein formaldehyde is converted to formic acid and formic acid is converted to carbon dioxide and water at atmospheric pressure and at a temperature in the range from about 50° C. about 90° C.

24. The method of claim 19 wherein the oxidation is carried out at a pressure ranging from atmospheric to about 200 psi.

25. The method of claim 19 further comprising agitating said stream to achieve and maintain a level of dissolved oxygen with the range of about 1 ppm to about 7 ppm.

* * * * *